United States Patent [19]

Lundblad et al.

[11] 4,186,192
[45] Jan. 29, 1980

[54] STABILIZED IMMUNE SERUM GLOBULIN

[75] Inventors: John L. Lundblad, El Cerrito; Willis L. Warner, San Rafael; Peter M. Fernandes, Concord, all of Calif.

[73] Assignee: Cutter Laboratories, Inc., Berkeley, Calif.

[21] Appl. No.: 970,686

[22] Filed: Dec. 18, 1978

[51] Int. Cl.² ............ A61K 39/00; A61K 35/14; A61K 37/00
[52] U.S. Cl. .................... 424/85; 424/101; 424/177
[58] Field of Search ............ 424/177, 101, 85

[56] References Cited

U.S. PATENT DOCUMENTS 4,089,944  5/1978  Thomas .................. 424/101

OTHER PUBLICATIONS

Chem. Abstr. 80, 1974, 124750r.
Chem. Abstr. 77, 1972, 52306p.
Chem. Abstr. 87, 1977, 150657e, 150658f, 150659g.

Primary Examiner—Delbert R. Phillips
Attorney, Agent, or Firm—James A. Giblin; Robert E. Allen; Bertram Bradley

[57] ABSTRACT

Composition comprising an aqueous solution of immune serum globulin and maltose, the amount of maltose being sufficient to inhibit "shedding" of the globulin with time.

20 Claims, 2 Drawing Figures

STABILIZED IMMUNE SERUM GLOBULIN

BACKGROUND OF THE INVENTION

1. Field

This disclosure is concerned generally with immune serum globulin (ISG) preparations and specifically with a highly stabilized immune serum globulin solution.

2. Prior Art

It is well known that many plasma protein preparations intended for administration to humans or animals require stabilizers to prevent denaturation or other alteration prior to use. Instability of protein preparations is particularly observed as a function of concentration. Some, like immune serum globulin preparations, are particularly unstable in relatively dilute solutions (e.g. under 15 wt % concentration) of the protein. This instability, which may be manifest by the formation of insoluble particles ("shedding"), is often increased when storage of the protein preparation is at temperatures higher than refrigerator temperature (about room temperature or higher).

Various additives for stabilizing protein preparations have been used with varying degrees of success. For example, increasing the concentration of the protein or adding another protein such as albumin has enhanced stability in some cases. Unfortunately, however, such preparations may not always be acceptable for therapeutic purposes. It is known that amino acids are useful in stabilizing some protein preparations and degraded gelatin is commonly used as a stabilizer, especially in European countries. In considering an appropriate stabilizer, consideration should be given to such factors as lack of antigenicity (possible with gelatin), effect on osmolarity of the final solution, biological activity of the specific proteins being stabilized, and the availability and cost of the stabilizer.

Various carbohydrates have been used to stabilize, facilitate processing, and/or enhance the solubility of certain biologically active protein preparations. For example, U.S. Pat. No. 2,826,533, to Fowell discloses the use of dextrose to increase the solubility of a fibrinogen preparation. U.S. Pat. No. 4,089,944 to Thomas discloses the use of a variety of carbohydrates (e.g. dextrose, mannose, galactose, fructose, lactose, sucrose, and maltose) to increase the solubility of an AHF-fibrinogen composition. The stabilization of plasma with invert sugar is disclosed in U.S. Pat. No. 3,057,781 to Mace et al.

Although dextrose has been added to immune serum globulin (e.g. Intraglobin ®, a modified immune serum globulin) to enhance stability and/or solubility, it has been found that, with time, the globulins in commercially available samples tend to aggregate, thereby increasing the optical density and resulting in a phenomenon commonly referred to as "shedding". As used herein, "shedding" means a visible precipitation of protein molecules. It is thought that shedding is caused by aggregation of the globulin molecules, rendering the molecules insoluble, especially in dilute solution. However, it should be noted that the exact nature of shedding is not fully understood. Shedding is undesirable since it is visually observable and indicates the possibility of inactivation or denaturation of the shedded protein and, hence, lessens the effective amount of globulin available. In addition a solution of globulin having shedded protein is unsatisfactory as a product in terms of visual appearance.

Another disadvantage associated with the use of known sugars as stabilizers in protein solutions is the fact that some sugar solutions tend to brown on heating. In addition, in some instances, it may be desirable to avoid the use of rapidly assimilated sugars such as dextrose in products intended for human use, especially for use in diabetic patients.

Quite surprisingly, we have developed a stabilized immune serum globulin preparation substantially free of shedding in dilute concentration over prolonged periods of time which utilizes a common, relatively inert sugar which, in general, can be used in amounts sufficient to assure a pharmaceutically acceptable isotonic globulin solution. This sugar can be used to stabilize immune serum globulin (ISG) preparations suitable for intramuscular administration (IMGG) or specially treated to render it suitable for intravenous administration (IVGG). Details of our stabilized preparations are disclosed herein.

SUMMARY OF THE INVENTION

Our stabilized immune serum globulin preparation comprises an aqueous solution of a therapeutically effective amount of molecules of immune serum globulin (ISG) and maltose, the amount of maltose being sufficient to inhibit substantially the shedding of the globulin molecules with time. In one preferred embodiment, the preparation comprises a sterile, pharmaceutically acceptable solution of about 16.5 weight percent IMGG or 5 to 10 weight percent IVGG and maltose, the maltose being present in an amount to assure pharmaceutically acceptable isotonicity of the globulin solution. In another preferred embodiment the globulin solution includes about 2.5 to about 18 wt. % (preferably about 5 to 15 wt. %) of the maltose, a very preferred amount of maltose being about 10 weight percent. In yet another preferred embodiment the solution includes about 10 weight percent maltose and an amount of glycine, preferably about 0.1 M glycine.

SPECIFIC EMBODIMENTS

Figure 1:
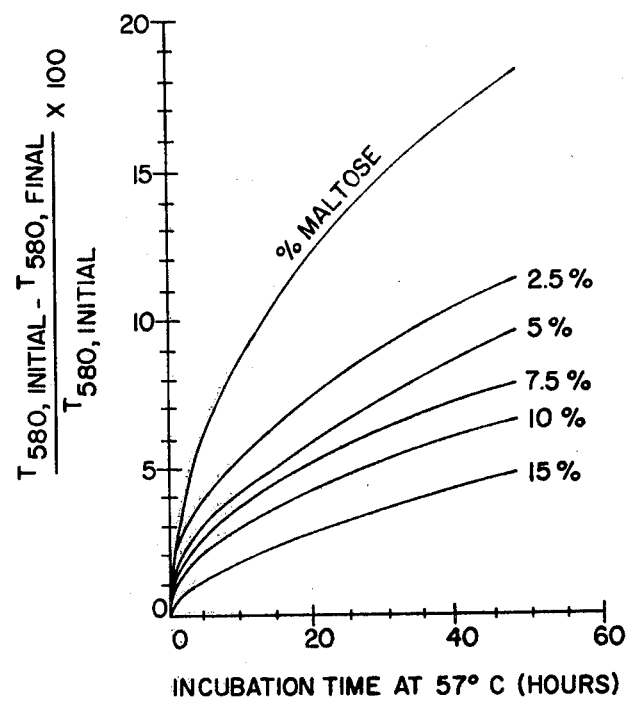
FIG. 1 is a graph illustrating the stability of an IVGG solution as a function of time and maltose concentration at 57° C.

The stabilizing agent of this disclosure is especially useful for lower concentration solutions of ISG (IMGG or IVGG) where, because of a relatively small amount of protein, shedding is more likely and apparent.

The immune serum globulin (IMGG) or immune serum globulin modified for intravenous injection (IVGG) are well known and can be prepared by known means. For example the IMGG (frequently available as a 16.5 wt. % solution) is commonly prepared via Cohn fractionation (see, Cohn et al, J. Am. Chem. Soc., 68, 459-475 (1946); Oncley et al, J. Am. Chem. Soc. 71, 541-550 (1949)). Examples of preparing an IVGG are disclosed in U.S. Pat. No. 3,903,262 to Pappenhagen et al. The specific disclosures of the above publications are incorporated herein by reference thereto.

The maltose used to stabilize the aqueous globulin solutions is described in detail in, for example, The Merck Index, Ninth Edition, Merck & Co., Inc., Rahway, N.J. (1976). The disaccharide maltose is readily available in pure form and has good stability in aqueous solutions up to 20 weight percent which can be autoclaved without browning of the solution. Physiologically in small quantities it is practically inert. When administered intravenously, it is partially converted to glucose by the specific enzyme maltase found in many tissue sites in most animal species, including humans.

Some administered maltose is rapidly excreted by the human kidney unchanged without significant diuresis. The conversion to glucose is gradual and frequently undetectable when plasma glucose is serially measured; there is no apparent increase in circulating insulin levels. No adverse reactions have been reported, even after the administration of up to 200 grams of maltose in four hours as a 10% aqueous solution. Since maltose is a disaccharide, a 10% solution is approximately isotonic in humans. As used herein, the expression pharmaceutically acceptable isotonicity refers to that range of osmolality in a pharmaceutical solution which, in general, will not result in significant local adverse effects (e.g. vessel wall irritation). Although the amount of maltose needed to assure an osmolality within this range will vary depending on such factors as amino acid concentration, salt concentration, etc., in general, we prefer using about 5 to 15 weight percent maltose in the IMGG or IVGG solution, preferably about 10 weight percent.

More important however in determining the proper amount of maltose is the need to avoid shedding in the IMGG or IVGG solution with time. As noted above, shedding is a term referring to a noticeable precipitation of the globulin molecules, especially prevalent as the concentration of the protein solution is decreased. The phenomenon of shedding can be accurately observed and recorded by noting the spectrophotometric transmittance of light at 580 nm of a given solution. Differences in transmittance with and without varying amounts of the maltose provide a means of determining the degree of shedding over a period of time at a given temperature. Shedding can also be noted visually. As used herein, the substantial inhibition of shedding means a change in transmittance at $T_{580}$ of less than 10%, preferably less than 5% when the solution is heated for 24 hours at 57° C. It can be appreciated that shedding will occur more slowly at lower temperatures.

In preliminary studies directed toward understanding the nature of the shedding phenomenon, it was found that variation in the final container pH of a 5% IVGG solution in the allowable range, pH 6.4 to 7.2, had no effect on the degree of shedding. Further studies indicated that non-carbohydrate addition such as NaCl or glycine alone were not effective in stabilizing the protein solution for more than a very short period. A combination of NaCl and glycine was also not effective.

From the above studies, it becomes apparent that the accelerated precipitation test offered a simple and rapid test of the ability of IMGG or IVGG to resist instability due to storage under adverse conditions, as well as an indication of the extent to which the character of the molecule had been preserved.

A variety of carbohydrates at varying concentrations were investigated (i.e. dextrose, fructose, mannitol, sorbitol and maltose) as potential stabilizers for the protein solution. In all cases, stability appeared to be directly proportional to sugar concentration. In all cases the final container material was more clear using the carbohydrates than preparations which included glycine and NaCl.

It was found that maltose was the best overall stabilizer for clinical acceptability. For example, dextrose can cause undesirable hyperglycemia; mannitol is a diuretic at effective concentrations; and sorbitol and fructose have adverse effects in acid-base balance.

In a series of experiments in which the amount of maltose was increased from 5% to 18%, it was also found that the addition of glycine significantly improved the clarity of a 5% IVGG solution. Thus, although the maltose addition results in a stable product, substantially free from shedding, in a very preferred embodiment glycine is included (e.g. about 0.1 M glycine for a 5% IVGG solution). The data summarizing the effects of maltose, glycine, and combination of the two on IVGG clarity are summarized in the table below.

Table I

Effect of Maltose and Maltose-Glycine on IVGG Clarity

| Additive | Initial $T_{580\%}$ | Final $T_{580\%}$ | % Change |
|---|---|---|---|
| 5% Maltose | 99.05 | 95.69 | 3.39 |
| 7% Maltose | 99.25 | 96.51 | 2.76 |
| 10% Maltose | 99.35 | 97.24 | 2.13 |
| 13% Maltose | 99.25 | 97.87 | 1.39 |
| 18% Maltose | 99.45 | 98.07 | 1.39 |
| 5% Maltose, 0.1M Glycine | 99.15 | 97.29 | 1.88 |
| 7% Maltose, 0.1M Glycine | 99.35 | 97.58 | 1.78 |
| 10% Maltose, 0.1M Glycine | 99.35 | 98.22 | 1.14 |
| 13% Maltose, 0.1M Glycine | 99.50 | 98.76 | 0.75 |
| 18% Maltose, 0.1M Glycine | 99.60 | 98.76 | 0.85 |
| 5% Maltose, 0.3M Glycine | 99.15 | 98.07 | 1.09 |
| 7% Maltose, 0.3M Glycine | 99.35 | 98.66 | 0.70 |
| 10% Maltose, 0.3M Glycine | 99.45 | 98.96 | 0.50 |
| 13% Maltose, 0.3M Glycine | 99.45 | 99.05 | 0.40 |
| 18% Maltose, 0.3M Glycine | 99.65 | 99.25 | 0.40 |

It should be pointed out that maltose is an especially preferred stabilizer since it is a relatively harmless sugar and sufficient data are available on its toxicological and clinical effects. Glycine in combination with maltose does improve clarity and is a commonly used stabilizer for protein solutions. Because of this and since glycine also contributes to the osmolality of the product, it was found that a preferred solution should contain only 0.1 M glycine and 10% maltose. Osmolality values for some maltose-glycine formulations which supported the above findings are summarized in the table below.

Table II

Effect of Additive on Osmolality of 5% IVGG Solution

| Additive plus 5% IVGG | Osmolality, mOsm/kg |
|---|---|
| 10% Maltose, 0.3M Glycine | 466 |
| 10% Maltose, 0.1M Glycine | 366 |
| 10% Maltose | 300 |
| 0.3M Glycine, 0.45% NaCl | 413 |

Figure 2:
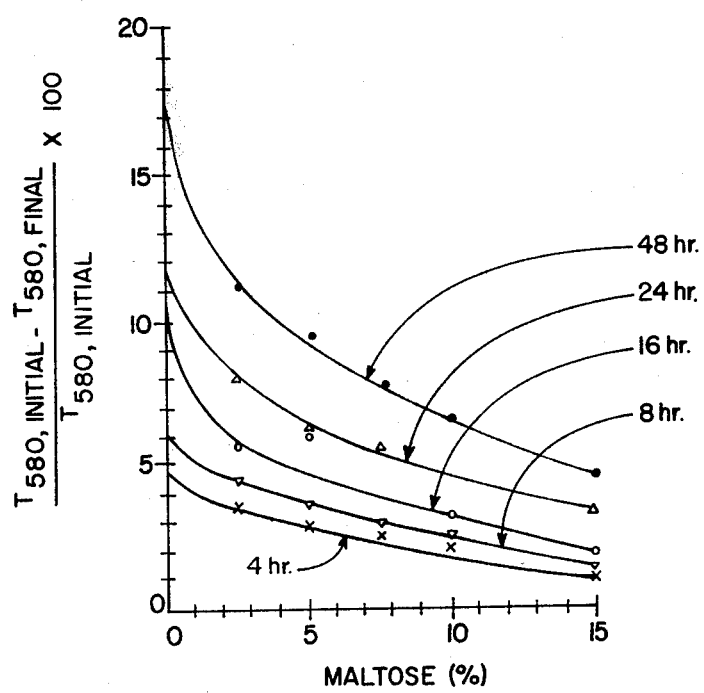
FIG. 2 is a graph further illustrating the beneficial effects of increasing amounts of maltose on the stability of an IVGG solution over a period of time at 57° C.

The beneficial effects of increasing maltose concentrations on the long term stability (accelerated studies using the temperature of 57° C.) are summarized in FIGS. 1 and 2 where the change in absorbance at $T_{580}$ as functions of maltose concentrations and time at 57° C. is dramatically illustrated. From FIG. 1 it can be seen that shedding was substantially inhibited with as little as about 2.5% maltose.

EXAMPLE

The preparation of the product of this disclosure in a very preferred embodiment using the best methodology known to date is illustrated for a specific 5% IVGG solution below. It can be appreciated, however, that those skilled in the art in view of this disclosure will now be able to prepare readily any stabilized ISG or IVGG solution. Our illustrative stabilized product was prepared as follows:

15 grams of Cohn Fraction II paste are suspended in a 0.45% sodium chloride solution at 0–5° C. such that the concentration of protein is 5±0.2%.

The solution (approximately 100 ml) is warmed to 22–25° C. and the pH adjusted to 8.1±0.1 with 1 N sodium hydroxide. 0.387 g/L of solution of Dithiothreitol (Aldrich Chemical Company, Milwaukee, Wis.) is added and the ensuing chemical reduction is allowed to proceed for 15 minutes. Iodoacetamide (Aldrich Chemical Company) is then added at a concentration of 1.018 g/L of solution and the alkylation process is allowed to occur for 60 minutes. The pH of the solution is maintained at 8.1±0.1 by addition of 1 M sodium hydroxide or 0.8 M sodium acetate buffer.

The pH is reduced to 6.8 on completion of the protein modification process and the solution subjected to extensive diafiltration for removal of residual reagents. This process consists of diafiltering the protein solution for at least a total of seven volume replacements against the following solutions:

0.45% sodium chloride for the first three replacements.

Water for injection for a minimum of four replacements.

The solution is clarified using a non-asbestos containing filter and maltose and glycine added such that the final composition contains:

Protein—5%
Maltose—10%
Glycine—0.75% (0.1 M)

The pH of the solution is adjusted to 6.8±0.1 and the material is sterile filtered through a 0.2 micron filter and filled into appropriate final containers.

Inasmuch as the above described disclosure is subject to numerous variations which are or will become apparent to those skilled in the art, it is intended that the disclosed examples be construed as illustrative only and that the described invention be limited only by the following claims.

We claim:

1. A stabilized immune serum globulin preparation comprising an aqueous solution of a therapeutically effective amount of molecules of ISG and maltose, the amount of maltose being sufficient to inhibit shedding of the globulin over prolonged periods of time.

2. The preparation of claim 1 wherein the amount of maltose ranges from about 2.5 to about 18 weight percent.

3. The preparation of claim 2 wherein the amount of maltose ranges from about 5 to about 15 weight percent.

4. The preparation of claim 3 wherein the amount of maltose is about 10 weight percent.

5. The preparation of claim 1 wherein the solution includes glycine.

6. The preparation of claim 5 wherein the glycine is present in a concentration of about 0.1 M.

7. The preparation of claim 1 wherein the globulin present is IMGG, and the amount of the globulin is about 16.5 wt. %.

8. The preparation of claim 1 wherein the globulin is IVGG, and the amount of the globulin is about 5 wt. %.

9. The preparation of claim 1 wherein amount of maltose is sufficient to assure pharmaceutically acceptable osmolality.

10. The preparation of claim 9 wherein the osmolality of the solution ranges from about 170 to 600 mOsm/kg.

11. The preparation of claim 10 wherein the osmolality is about 260 to 500 mOsm/kg.

12. A sterile, pharmaceutically acceptable preparation comprising an aqueous solution of molecules of an immune serum globulin, the globulin having been modified for intravenous administration, and maltose, the maltose being present in an amount sufficient to inhibit substantial shedding of the globulin molecules.

13. The preparation of claim 12 wherein the amount of maltose is sufficient to inhibit visually detectable shedding.

14. The preparation of claim 12 wherein the amount of maltose ranges from about 2.5 to about 18 wt. %.

15. The preparation of claim 14 wherein the amount of maltose ranges from about 5 to about 15 wt. %.

16. The preparation of claim 15 wherein the amount of maltose is about 10 wt. %.

17. The preparation of claim 16 wherein the aqueous solution includes about 5 weight percent of the globulin.

18. The preparation of claim 12 wherein the solution includes glycine.

19. The preparation of claim 18 wherein the glycine concentration is about 0.1 M.

20. The preparation of claim 12 wherein the solution has a pharmaceutically acceptable osmolality.

* * * * *

UNITED STATES PATENT AND TRADEMARK OFFICE
CERTIFICATE OF CORRECTION

PATENT NO. : 4,186,192

DATED : January 29, 1980

INVENTOR(S) : PETER M. FERNANDES, JOHN LUNDBLAD, WILLIS L. WARNER

It is certified that error appears in the above-identified patent and that said Letters Patent are hereby corrected as shown below:

On the information-bearing front page, the inventors names should appear as follows:

Inventors:  Peter M. Fernandes, Concord;
   John L. Lundblad, El Cerrito;
   Willis L. Warner, San Rafael,
   all of California.

Signed and Sealed this

Twentieth Day of May 1980

[SEAL]

Attest:

SIDNEY A. DIAMOND

Attesting Officer     Commissioner of Patents and Trademarks